US011136278B2

(12) United States Patent
Choi

(10) Patent No.: US 11,136,278 B2
(45) Date of Patent: Oct. 5, 2021

(54) CONVERSION OF PROPYLENE TO ETHYLENE

(71) Applicant: LUMMUS TECHNOLOGY LLC, Bloomfield, NJ (US)

(72) Inventor: Sukwon Choi, Clifton, NJ (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 17/100,698

(22) Filed: Nov. 20, 2020

(65) Prior Publication Data

US 2021/0147319 A1    May 20, 2021

Related U.S. Application Data

(60) Provisional application No. 62/937,992, filed on Nov. 20, 2019.

(51) Int. Cl.
*C07C 4/06* (2006.01)
*C07C 11/08* (2006.01)
*C07C 11/04* (2006.01)

(52) U.S. Cl.
CPC .............. *C07C 4/06* (2013.01); *C07C 11/04* (2013.01); *C07C 11/08* (2013.01)

(58) Field of Classification Search
CPC .......... C07C 11/04; C07C 11/08; C07C 4/06; C07C 6/04; C07C 11/06; C07C 11/10
See application file for complete search history.

(56) References Cited

U.S. PATENT DOCUMENTS 5,026,935 A   6/1991  Leyshon et al.
5,990,369 A  11/1999  Barger et al.
(Continued)

FOREIGN PATENT DOCUMENTS

| CN | 107973684 A | 5/2018 |
| JP | 2016-117667 A | 6/2016 |
| WO | 2015/077338 A1 | 5/2015 |

OTHER PUBLICATIONS

International Search Report issued in PCT/US2020/061640 dated Mar. 12, 2021 (4 pages).
(Continued)

*Primary Examiner* — Sharon Pregler
(74) *Attorney, Agent, or Firm* — Osha Bergman Watanabe & Burton LLP

(57) ABSTRACT

Processes and systems for the conversion of propylene to ethylene may include introducing a propylene feed stream to a C3 metathesis reactor, converting the propylene to ethylene and 2-butene. The metathesis reactor effluent may be recovered and separated in a fractionation system to recover an ethylene product, a C3 fraction, a C4 fraction, and a C5+ fraction. All or a portion of the C3 fraction may be fed to the C3 metathesis reactor to produce additional ethylene. The C4 fraction may be converted in a C4 isomerization/metathesis reaction zone by: (i) isomerization of 2-butenes to 1-butene, (ii) metathesis of the 1-butene and 2-butene to produce propylene and 2-pentene, and/or (iii) autometathesis of the 1-butene to produce ethylene and 3-hexene. An effluent from the C4 isomerization/metathesis reaction zone may then be recovered and fed from the C4 isomerization/metathesis reaction zone to the fractionation system.

23 Claims, 5 Drawing Sheets

(56) References Cited

U.S. PATENT DOCUMENTS 10,975,004 B2 * 4/2021 Shaikh ...................... C07C 2/10
2015/0141720 A1 * 5/2015 Ramachandran ..... C07C 5/2512
585/312

OTHER PUBLICATIONS

Written Opinion of the International Searching Authority issued PCT/US2020/061640 dated Mar. 12, 2021 (7 pages).

* cited by examiner

CONVERSION OF PROPYLENE TO ETHYLENE

FIELD OF THE DISCLOSURE

Embodiments herein relate to the conversion of propylene to ethylene. More specifically, embodiments herein relate to processes and systems for improving the conversion of propylene to ethylene via metathesis.

BACKGROUND

The products of propylene autometathesis are ethylene and n-butenes. Propylene metathesis creates one mole of ethylene (28 g/mol) from two moles of propylene (42 g/mol+42 g/mol). N-butenes (56 g/mol) as the second product is less valuable. On a mass basis, complete conversion of propylene results in only 33.3% of the propylene converting to ethylene, and the rest is n-butenes. This means if 100 tons of propylene feed were processed under the current commercial propylene metathesis process, approximately only 33.3 tons of ethylene would be produced, while resulting in 66.7 tons of 2-butenes.

SUMMARY OF THE DISCLOSURE

Systems and processes herein have now been developed to improve the conversion of propylene to ethylene via metathesis.

In one aspect, embodiments herein relate to processes for the conversion of propylene to ethylene. The processes may include introducing a propylene feed stream to a C3 metathesis reactor, and contacting the propylene with a metathesis catalyst in the C3 metathesis reactor to convert the propylene to ethylene and 2-butene. An effluent from the C3 metathesis reactor may be recovered and separated in a fractionation system to recover an ethylene product fraction, a C3 fraction, a C4 fraction, and a C5+ fraction. The process may also include: feeding all or a portion of the C3 fraction to the C3 metathesis reactor to produce additional ethylene, and feeding the C4 fraction to a C4 isomerization/metathesis reaction zone. The C4 fraction may be converted in the C4 isomerization/metathesis reaction zone by: (i) isomerization of a portion of the 2-butenes to 1-butene, (ii) metathesis of the 1-butene and 2-butene to produce propylene and 2-pentene, and/or (iii) autometathesis of the 1-butene to produce ethylene and 3-hexene. An effluent from the C4 isomerization/metathesis reaction zone may then be recovered, the effluent comprising ethylene, propylene, butenes, pentenes, and hexenes; and then fed from the C4 isomerization/metathesis reaction zone to the fractionation system.

In yet another aspect, embodiments herein relate to systems for the production of ethylene. The systems may include: a flow line for providing propylene from a feed source; a C3 metathesis reactor for contacting the propylene with a metathesis catalyst to convert the propylene to ethylene and 2-butene and recovering an effluent from the C3 metathesis reactor; a fractionation system for separating the effluent to recover an ethylene product fraction, a C3 fraction, a C4 fraction, and a C5+ fraction; a flow line for feeding all or a portion of the C3 fraction to the C3 metathesis reactor; a flow line for feeding the C4 fraction to a C4 isomerization/metathesis reaction zone; the C4 isomerization/metathesis reaction zone, for converting the C4 fraction by: (i) isomerization of a portion of the 2-butenes to 1-butene, (ii) metathesis of the 1-butene and 2-butene to produce propylene and 2-pentene, and/or (iii) autometath-esis of the 1-butene to produce ethylene and 3-hexene; a flow line for feeding an effluent from the C4 isomerization/metathesis reaction zone to the fractionation system, the effluent comprising ethylene, propylene, butenes, pentenes, and hexenes.

Other aspects and advantages will be apparent from the following description and the appended claims.

DETAILED DESCRIPTION

Figure 1:
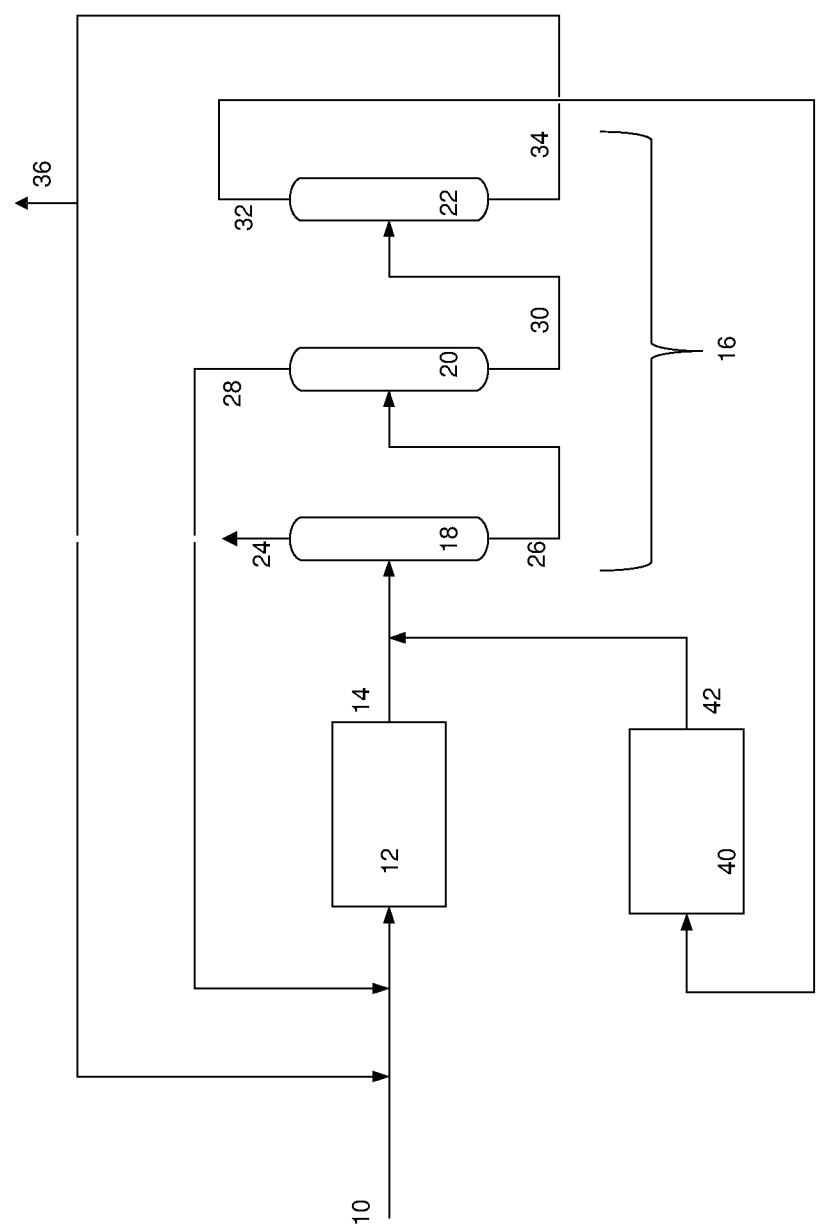
FIGS. 1-4 are simplified flow diagrams of processes according to embodiments herein.

Embodiments herein allow for increasing the ethylene product yield (total amount of ethylene produced per unit mass of propylene feedstock consumed) during propylene self-metathesis via the addition of a nC4s isomerization/metathesis reactor that can be operated such that essentially all propylene feed is converted into ethylene as the sole major product from various industrial propylene feedstocks, i.e., polymer, chemical, and refinery grades of propylene.

Embodiments herein achieve this via the introduction of a second reactor, a nC4s processing reactor, that primarily generates additional ethylene via: 1) initial double-bond isomerization of 2-butenes into 1-butene, and 2) subsequent self-metathesis of 1-butene. The by-products can be either separated as a product stream to be used elsewhere, or can be recycled back to the primary propylene metathesis reactor to either generate additional ethylene (via cross-metathesis with propylene) or nC4s that can be recycled back to the second reactor.

Embodiments herein addresses one of the key issues of the current commercial propylene metathesis process that exhibits a relatively low mass yield for the higher value ethylene at only 33.3 wt. %, with remainder 66.7 wt. % of mass ending up as lower value 2-butenes. Embodiments herein allow for some or all of the unwanted/lower-value 2-butenes by-product to be converted into the preferred/higher-value ethylene that significantly improves the overall economics of current propylene metathesis technology, making it more attractive as a process to produce ethylene.

Simplified process flow diagrams of systems and processes for conversion of propylene to ethylene according to embodiments herein are illustrated in FIGS. 1-4. As shown in the Figures, the overall process schemes involve two different primary reactors, a C3 (propylene) processing reactor and a nC4s (linear butenes) processing reactor.

Each of the primary reactors (C3 processing reactor and nC4s processing reactor) may include three (3) different types of reactors that may utilize one type of catalyst or two different types of catalysts: (I) metathesis only, (II) isomerization followed by metathesis, or (III) isomerization followed by mixed isomerization plus metathesis. All three different reactor types can be used for the C3 processing reactor, while the nC4s processing reactor can be of Types II or III according to embodiments herein.

Below is a list of all major reactions that are involved in the newly proposed process schemes according to embodiments herein.

Reaction 1: $1C_3 + 1C_3 \leftrightarrow 1C_2 + 2C_4$

Reaction 2: $1C_3 + 2C_5 \leftrightarrow 1C_4 + 2C_4$

Reaction 3: $1C_3 + 3C_6 \leftrightarrow 2C_5 + 1C_4$ $2C_5 \leftrightarrow 1C_5$  Reaction 4:

$3C_6 \leftrightarrow 2C_6$  Reaction 5:

$2C_6 \leftrightarrow 1C_6$  Reaction 6:

$1C_3 + 1C_5 \leftrightarrow 1C_2 + 2C_6$  Reaction 7:

$1C_3 + 2C_6 \leftrightarrow 2C_4 + 1C_5$  Reaction 8:

$1C_3 + 1C_6 \leftrightarrow 1C_2 + 2C_7$  Reaction 9:

$2C_4 \leftrightarrow 1C_4$  Reaction 10:

$1C_4 + 2C_4 \leftrightarrow 1C_3 + 2C_5$  Reaction 11:

$1C_4 + 1C_4 \leftrightarrow 1C_2 + 3C_6$  Reaction 12:

Other reactions are also possible, such as the reaction of 1-butene, such as may be produced in the C3 processing reactor when containing isomerization catalyst, and the subsequent reaction of the 1-butene with propylene to produce ethylene and 2-pentene within the same reactor. However, as there are many permutations and possibilities for reaction, only the twelve reactions of primary interest to the propylene and butene reaction zones are listed in the twelve reaction schemes above. Depending on the specific reactor configuration type selected for each of the C3 and C4 reactors, different sets of reactions become relevant. The relevant reaction sets associated with each specific reactor configuration type is summarized in Table 1.

TABLE 1

List of relevant reactions for each specific reactor type

| Reactor Type | | Main Reactions (Rxn #) |
|---|---|---|
| A | A-I | 1, 2, 3 |
|   | A-II | 1, 2, 3, 4, 5, 6, 7, 8, 9 |
|   | A-III | 1, 2, 3, 4, 5, 6, 7, 8, 9 |
| B | B-II | 10, 11, 12 |
|   | B-III | 10, 11, 12 |

Furthermore, it should also be noted that any combination of reactor configurations between the different types for reactors A and B may be employed; e.g., (A-II+B-III) or (A-I+B-II); and will depend on the specific needs of the producer and/or site constraints.

Reaction 1, as noted above, is propylene autometathesis. Reactions 7, 9, and 12 also occur in processes according to embodiments herein, each producing additional ethylene not produced in propylene autometathathesis. Further, additional reactions enabled by the flow schemes allow essentially all byproducts (nC4s, nC5s, and nC6s) to be recycled-, with the exception of 2-heptenes byproduct from Reaction 9, which may be purged with a heavies C5+ stream to keep its concentration minimum in the recycle loop, when used. It should also be noted that the 2-heptene byproduct only forms for cases using the Type II and Type III reactor configurations for Reactor A, and should be minimal as 1-hexene is the least favored nC6 isomer at equilibrium.

Referring now to FIG. 1, a simplified process flow diagram for producing primarily ethylene from a propylene feed stream, according to embodiments herein, is illustrated. A fresh propylene feed stream 10 is fed to a propylene metathesis reactor 12. In metathesis reactor 12, propylene reacts via autometathesis to form ethylene and 2-butene. A reaction effluent 14 may then be recovered from C3 reactor 12. Effluent 14 may contain unreacted propylene, as well as reaction products ethylene and 2-butene.

As described above and illustrated in FIG. 1A, the reactor types (I), (II) and (III) may be used in embodiments herein, where reactor type (I) contains one or more reactors or catalyst zones 1 containing a metathesis catalyst. Reactor type (II) may include segregated reaction zones 2 and 3, including a first reactor or catalyst zone (bed) 2 containing an isomerization catalyst, followed by a second reactor or catalyst zone (bed) 3 containing a metathesis catalyst. Reactor type (III) includes segregated reaction zones 4 and 5, where reaction zone 4 is a reactor or catalyst bed containing an isomerization catalyst and reaction zone 5 is a reactor or catalyst bed containing a mixture of isomerization and metathesis catalyst. Mixed catalyst systems may be formed by admixture of the two types of catalyst, or may be formed by use of a bifunctional catalyst, for example.

Due to recycle, discussed below, and possible inclusion of isomerization catalyst where reactor 12 is a Type II or Type III reactor, reaction effluent 14 may also include pentenes and hexenes, among other reaction byproducts. Primary reactions occurring in reactor 12 may include Reaction 1 for a Type I reactor, Reactions 1, 2, and 3 for a Type II reactor, and each of Reactions 1-9 for a type III reactor.

Reaction effluent 14 may be fed to a separation system 16, which may include one or more distillation columns for fractionation of the reaction effluent into two or more fractions. As illustrated in FIG. 1, separation system 16 includes a deethanizer 18, a depropanizer 20, and a debutanizer 22. Deethanizer 18 may be used to separate reaction effluent 14 into an ethylene product fraction 24 and a C3+ fraction 26. The C3+ fraction may then be fed to depropanizer 20 for separation into a C3 overhead fraction 28 and a C4+ bottoms fraction 30. The C4+ bottoms fraction may then be fed to debutanizer 22 for separation into a C4 overhead fraction 32 and a C5+ bottoms fraction 34.

The C3 overhead fraction 28 and the C5+ bottoms fraction 34 may be recycled back to reactor 12 for further conversion and production of ethylene. Continued isomerizaton and reaction of C5s may result in the production of C6s and C1s, which may be purged from the system via a C5+ purge 36. Alternatively, a dehexanizer (not shown) may be used to separate a heavies purge stream from the recycled C5s and C6s. Further, where the feed stream is a dilute propylene, a small C3 purge stream (not shown) may be used to avoid unwanted buildup of propane or other impurities in the system.

Figure 1A:
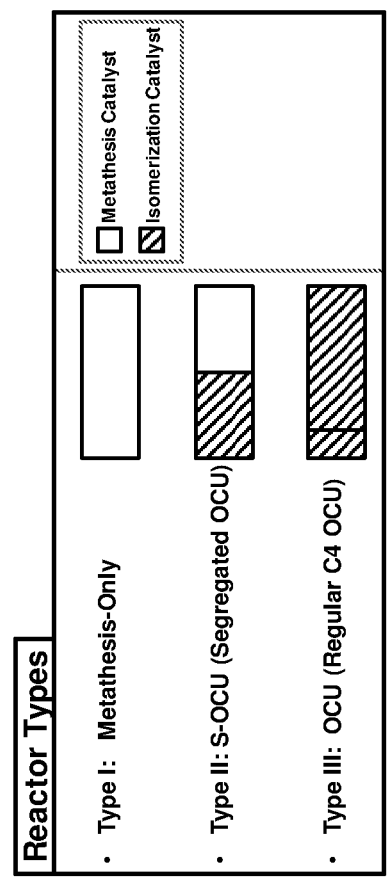

C4 overhead fraction 32, containing primarily 2-butenes, may then be fed to C4 reaction zone 40, which may include both an isomerization catalyst and a metathesis catalyst, in the same or different reaction beds, zones or reactors (Types (II) or (III) reactors), as illustrated with respect to FIG. 1A and described above. In reaction zone 40, primary reactions occurring may include Reactions 10, 11, and 12, converting the 1-butene and 2-butene to ethylene, propylene, 2-pentene, and 3-hexene. Isomerization of the reaction products and/or continued reaction may result in other reaction products as well. The effluent 42 recovered from reaction zone 40 may thus include a mixture of C2-C6+ hydrocarbons, and may be mixed with the effluent 14 from reactor 12 for separation in separation zone 16, where the C5s and C6s produced in reaction zone 40 may be recovered and further processed in reactor 12 to produce ethylene via Reactions 7 and 9.

Figure 2:
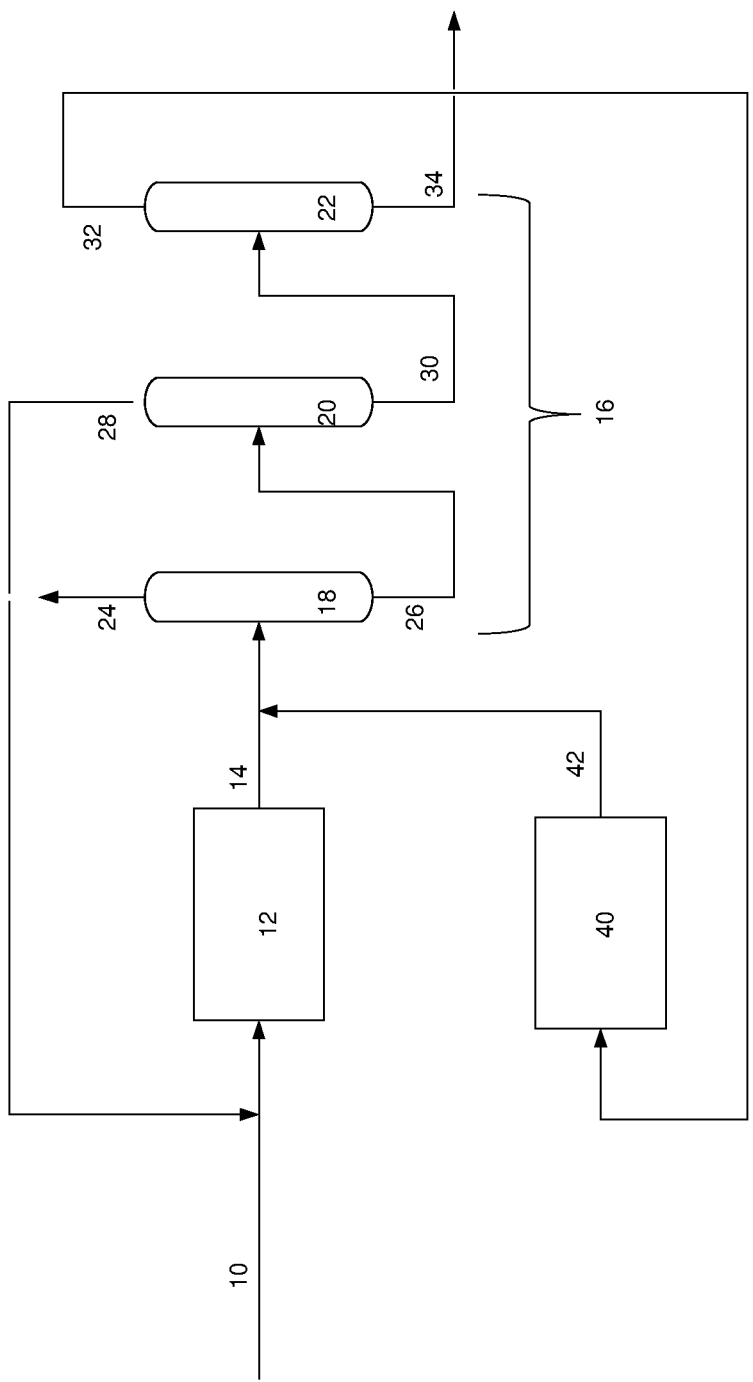

In some embodiments, the nC5s and nC6s formed in Reactor B are not recycled, but instead are removed as a product stream that can be used for other purposes, such as a gasoline blendstock or feed to a steam cracker, among others. The options for reactor configuration types remain the same in these embodiments as with cases that include recycling of the nC5s and nC6s process streams: all three (3) different reactor types can be used for Reactor A, while Reactor B can be of Types II or III. Such an embodiment is illustrated in FIG. 2, where like numerals represent like parts. The C3 feed 10 is processed in C3 reactor 12, the C4 overhead fraction 32 is processed in C4 reaction zone 40, and the C5+ bottoms 34 may be recovered as a product for gasoline blending or for feed to a steam cracker (not shown) for production of additional ethylene and propylene. In some embodiments, the steam cracker effluent separations may be integrated with fractionation system 16.

Figure 3:
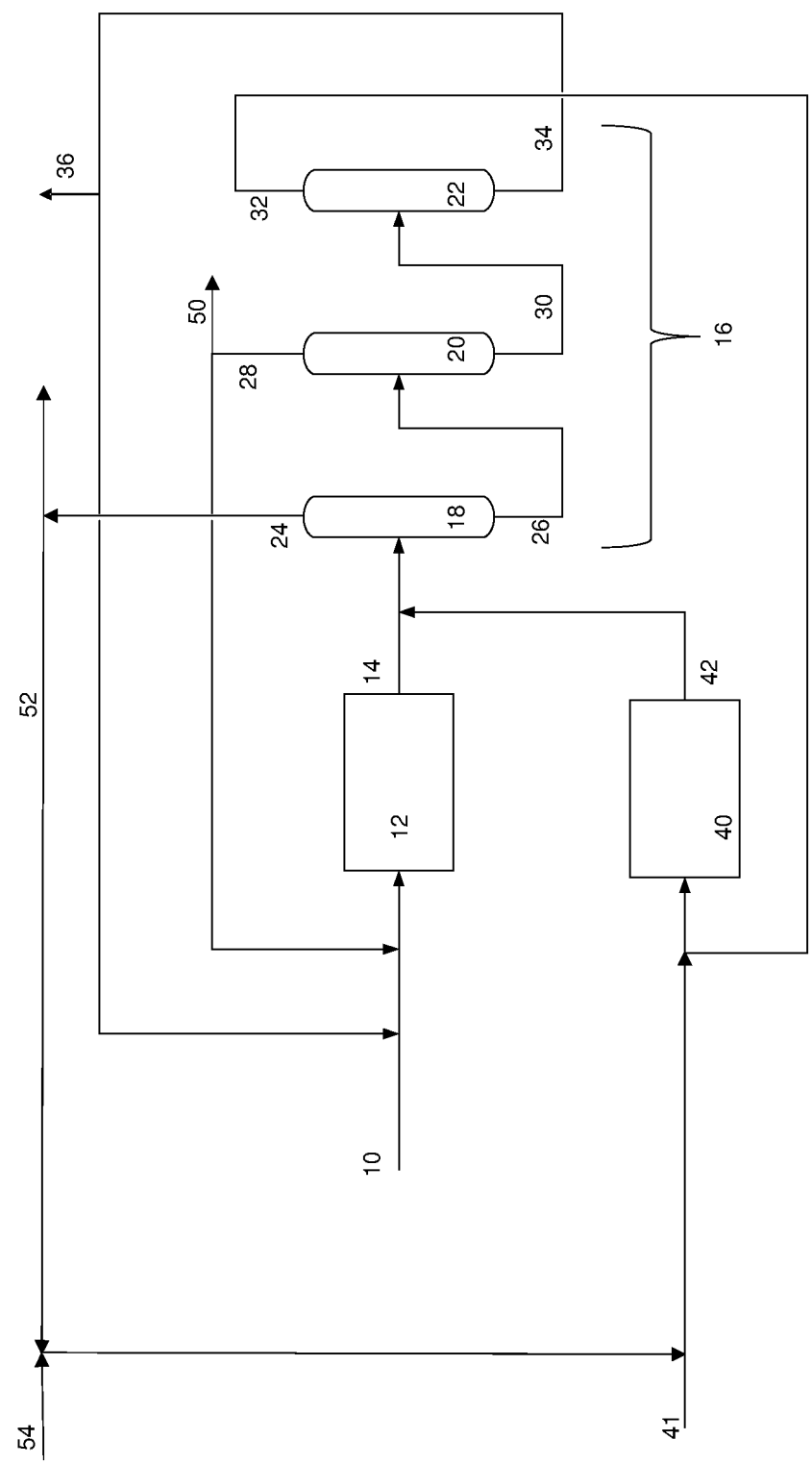

In some embodiments, a fresh mixed C4 fraction, containing n-butenes, may additionally be processed in reaction zone 40. It is further recognized that market demand may vary, and it may be desirable to vary the product yield profiles among the key light olefins (C2/C3/C4), which may be used as raw materials at the same facility or may be sold as products. Referring now to FIG. 3, a system for varying the product yields of ethylene, propylene, and butenes according to embodiments herein is illustrated, where like numerals represent like parts.

A fresh propylene feed stream 10 is fed to a propylene metathesis reactor 12. In metathesis reactor 12, propylene reacts via autometathesis to form ethylene and 2-butene. A reaction effluent 14 may then be recovered from C3 reactor 12. Effluent 14 may contain unreacted propylene, as well as reaction products ethylene and 2-butene.

As described above, reaction effluent 14 may also include pentenes and hexenes, among other reaction byproducts. Reaction effluent 14 may be fed to a separation system 16, which may include one or more distillation columns for fractionation of the reaction effluent into two or more fractions. As illustrated in FIG. 3, separation system 16 includes a deethanizer 18, a depropanizer 20, and a debutanizer 22. Deethanizer 18 may be used to separate reaction effluent 14 into an ethylene product fraction 24 and a C3+ fraction 26. The C3+ fraction may then be fed to depropanizer 20 for separation into a C3 overhead fraction 28 and a C4+ bottoms fraction 30. The C4+ bottoms fraction may then be fed to debutanizer 22 for separation into a C4 overhead fraction 32 and a C5+ bottoms fraction 34.

The C3 overhead fraction 28 and the C5+ bottoms fraction 34 may be recycled back to reactor 12 for further conversion and production of ethylene. Continued isomerizaton and reaction of C5s may result in the production of C6s and C1s, which may be purged from the system via a C5+ purge 36. Alternatively, a dehexanizer (not shown) may be used to separate a heavies purge stream from the recycled C5s and C6s. Further, where the feed stream is a dilute propylene, a small C3 purge stream (not shown) may be used to avoid unwanted buildup of propane or other impurities in the system.

C4 overhead fraction 32, containing primarily 2-butenes, may then be fed to C4 reaction zone 40, which may include both an isomerization catalyst and a metathesis catalyst, in the same or different reaction beds, zones or reactors (Types (II) or (III) reactors), as illustrated with respect to FIG. 1A and described above. A fresh mixed C4 stream 41 may also be provided, the mixed C4 stream including 1-butene and 2-butene, such as a Raffinate I stream, for example.

In reaction zone 40, primary reactions occurring may include Reactions 10, 11, and 12, converting the 1-butene and 2-butene to ethylene, propylene, 2-pentene, and 3-hexene. Isomerization of the reaction products and/or continued reaction may result in other reaction products as well. The effluent 42 recovered from reaction zone 40 may thus include a mixture of C2-C6+ hydrocarbons, and may be mixed with the effluent 14 from reactor 12 for separation in separation zone 16, where the C5s and C6s produced in reaction zone 40 may be recovered and further processed in reactor 12 to produce ethylene via Reactions 7 and 9.

Flexibility in producing a desired proportion of ethylene, propylene, and butenes may be provided by including one or more of the following, as illustrated in FIG. 3. The system may include, for example, a propylene withdrawal stream 50, which may be used to recover a portion of the unreacted propylene from C3 overhead fraction 26. Alternatively, or additionally, an ethylene recycle stream 52 and/or a fresh ethylene feed stream 54 may be used to provide ethylene to C4 reaction zone 40, where the ethylene may react with the 2-butene to produce propylene. Where propylene is desired as a primary product, reactor 12 may be isolated (not used). Where ethylene is desired as a primary product, reactor 12 may be on-line, and the use of fresh mixed C4s 41 may be restricted.

Figure 4:
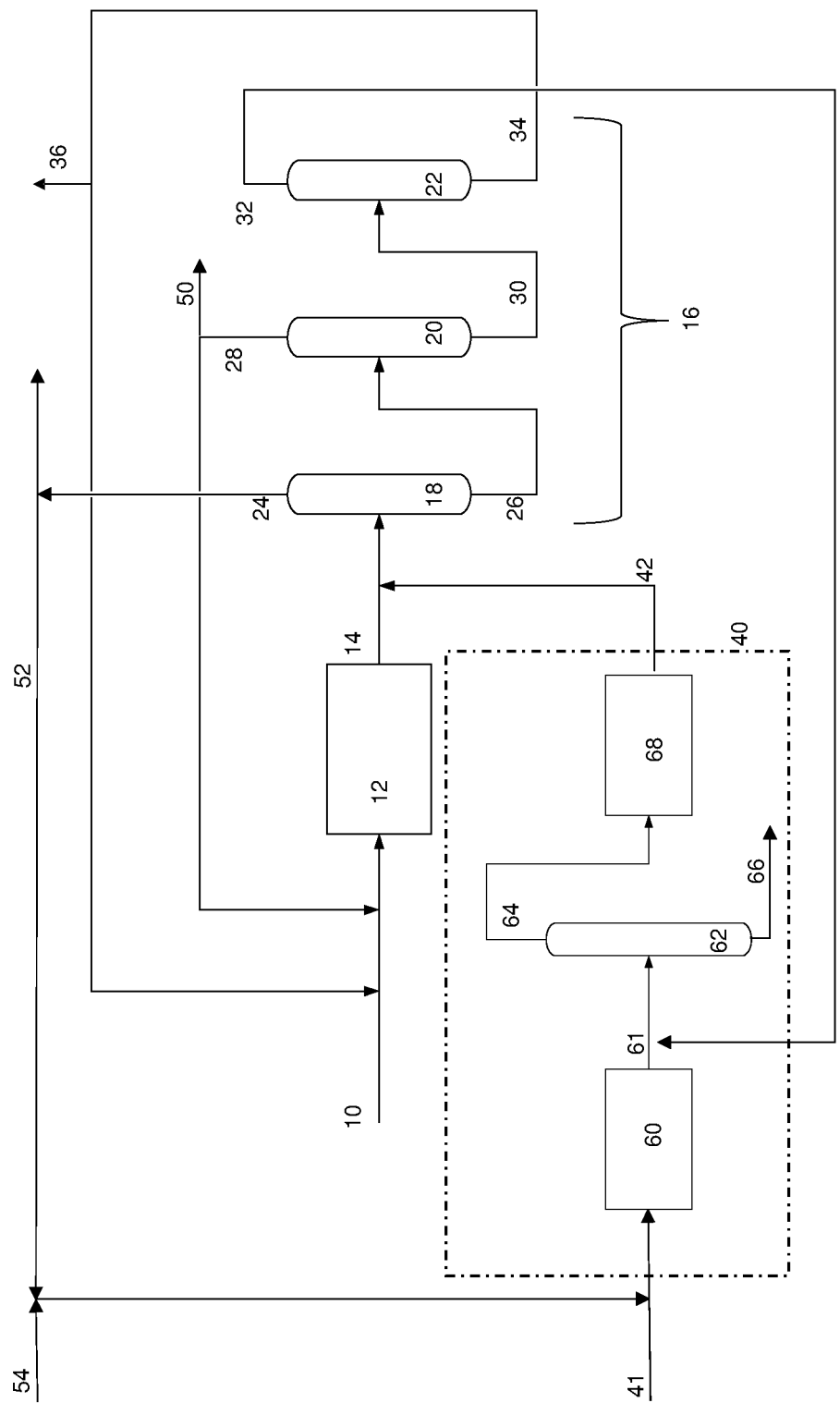

The nC4s processing reactor, in some embodiments, may be modified by (a) splitting Reactor B into two separator reactors, including a dedicated C4 isomerization reactor and a dedicated 1-butene autometathesis reactor, as illustrated in FIG. 4. Addition of a C4 superfractionator column between the reactors may be used to separate the 1-butene and 2-butene following isomerization, to improve the efficiency of the 1-butene autometathesis reactor to produce ethylene.

Referring now to FIG. 4, where like numerals represent like parts, C4 overhead fraction 32, similar to the embodiments in FIGS. 1-3, may be fed to C4 reaction zone 40. Reaction zone 40 may include a C4 isomerization reactor 60 for converting 2-butene to 1-butene, a superfractionator 62 for separating the effluent 61 into a 1-butene rich overheads fraction 64 from a 2-butene rich bottoms fraction 66, and a C4 metathesis reactor 68 for metathesis of the 1-butene overheads fraction 64 to produce ethylene and 3-hexene and recovery of C4 metathesis effluent 42. Depending upon the separation purity achieved in the C4 superfractionator, the selectivity for Reaction 12 may be greater than 80%, greater than 85%, or greater than 90%, in various embodiments. The 2-butene bottoms fraction 66 may be combined with the reactor feed for the C4 isomerization reactor 60 for further conversion to 1-butene.

Embodiments of the processes shown in FIG. 4 may additionally (optionally) allow n-butenes (nC4s) to be used as feedstock in addition to the propylene (C3) feedstock. The butane feedstock may be provided, as illustrated in FIG. 4, via flow line 41. Also, embodiments herein may use n-butenes (nC4s) as the primary feedstock (but not in the absence of C3) to produce ethylene relying less on propylene.

Embodiments of the processes and systems herein, as described above, may be used for the efficient and effective conversion of propylene to ethylene. In other aspects, embodiments herein provide for the flexible production of ethylene, propylene, and butenes, including isobutene.

C4 feed streams useful in embodiments herein may include steam cracker C4's or fluid catalytic cracker C4 steams. For steam cracker C4 streams, butadiene—as well as ethyl and vinyl acetylene are usually present. Butadiene is present in large quantities, e.g. around 40% of the C4 fraction. A selective hydrogenation unit is utilized to turn the butadiene into butene if butadiene is not desired as a product and also to hydrogenate the ethyl and vinyl acetylenes. If butadiene is desired as a product, it can be removed by extraction or another suitable process. The exit butadiene from extraction is typically on the order of 1 wt % of the C4 stream or less. To reduce butadiene to low levels (<1000 ppm), hydrogenation is required.

Propylene feed streams useful in embodiments herein may include dilute propylene streams, containing up to 50% propane, for example. In some embodiments, the propylene feed stream may include a low purity propylene feed, including 60-95 wt % propylene. In other embodiments, the propylene feed stream may include high purity propylene (95-99+ wt % propylene). A propane/propylene feed stream, in various embodiments, may contain at least 65 wt % propylene, at least 70 wt %, at least 75 wt %, at least 80 wt %, at least 85 wt %, at least 90 wt %, such as between 80 wt % and 95 wt %, or such as between 85 wt % and 90 wt % propylene, and may be fed to a metathesis reactor or reaction zone. In other embodiments, the propylene feed stream may be a polymer-grade propylene stream, which may have at least 98 wt %, at least 99 wt %, at least 99.5 wt %, or at least 99.8 wt % propylene.

Conditions in the metathesis reactor or the combined metathesis/isomerization reactor for the conversion of propylene to ethylene for metathesis may include temperatures in the range from 50° C. to 650° C., and pressures in the range from 0 barg to 40 barg. The reactors may be operated such that the reaction temperature is within the range from about 50° C. to about 600° C.; within the range from about 200° C. to about 450° C. in other embodiments; and from about 250° C. to about 400° C. in yet other embodiments. Pressures in the reactor may be, in some embodiments, between 5 and 15 bar, for example. The isomerization and metathesis reactions may be performed at a weight hourly space velocity (WHSV) in the range from about 2 to about 200 in some embodiments, and from about 6 to about 40 in other embodiments. Similar conditions may be used in the C4 and C5 isomerization/metathesis reaction zones.

The reactions may be carried out by contacting the olefin(s) with the isomerization and/or metathesis catalysts in the liquid phase or the gas phase, depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, propane, normal and branched C4, C5, alkanes and/or substantially inert gases, such as nitrogen and argon, may be present. For high product yield, the reactions may be conducted in the absence of significant amounts of deactivating materials such as water and oxygen.

The contact time needed to obtain a desirable yield of reaction products depends upon several factors such as the activity of the catalyst, temperature, pressure, and the structure of the olefin(s) to be isomerized and/or metathesized. Length of time during which the olefin(s) are contacted with catalyst can vary between 0.1 seconds and 4 hours, preferably from about 0.5 sec to about 0.5 hrs. The isomerization and metathesis reactions may be conducted batch-wise or continuously with fixed catalyst beds, slurried catalyst, fluidized beds, or by using any other conventional contacting techniques.

The catalyst contained within the metathesis reactors may be any known metathesis catalyst, including oxides of Group VIA, Group VIIA, and Group VIIIA metals on supports. Catalyst supports can be of any type and could include alumina, silica, mixtures thereof, zirconia, magnesia, titania, MOF (metal organic framework) compounds, and zeolites. In some embodiments, the metathesis catalyst is tungsten oxide on silica.

The double bond isomerization catalyst may be any known double bond isomerization catalyst. In some embodiments, the double bond isomerization catalyst may be one of magnesium oxide, calcium oxide, aluminum oxide, or mixed Mg—Al oxides (e.g, hydrotalcite-derived mixed oxides), among other possible catalysts.

In some embodiments, the double bond isomerization catalyst may be an alumina-titania catalyst. The catalyst may be a γ-alumina-titania crystalline mixture including active sites that catalyze the positional isomerization of olefins, and may be in the form of pellets, spheres, extrudates, and the like, and will typically have an effective diameter of 0.5 mm to 5 mm, such as in the range from 1 mm to 4 mm, or in the range from 2 mm to 3 mm. In some embodiments, the alumina-titania catalyst may have a composition of titanium with a lower limit of 0.01, 1, 2, 3, 4, 5, 10, 15, 20, or 25 to an upper limit of 15, 20, 25, 30, 35, 40, 45, or 50 wt %, where any lower limit may be combined with any upper limit. γ-Alumina-titania catalyst herein may have a surface area in some embodiments greater than 200 $m^2/g$, in other embodiments greater than 250 $m^2/g$, in other embodiments greater than 300 $m^2/g$, in other embodiments greater than 350 $m^2/g$, and in other embodiments greater than 400 $m^2/g$. The γ-alumina-titania catalysts may be tolerant of oxygenated species that are typically considered a poison, such as to MgO type catalysts, may act as an oxygenate scavenger protecting downstream catalyst beds, and in some embodiments may have activity for dehydration of alcohols in addition to isomerization activity. The γ-alumina-titania catalysts may also be more forgiving with respect to cyclopentene purity of the feed, and may allow greater than 5 wt %, greater than 7.5 wt %, or even greater than 10 wt % cyclopentene to be present in the feed, potentially negating typical upstream processes required to remove cyclopentene from the feed. These γ-alumina-titania catalysts may be used alone, such as in an isomerization only reactor or in an isomerization catalyst bed in a segregated olefin conversion unit (OCU), or may be used in admixture with other isomerization catalysts or metathesis catalysts.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the conversion of propylene to ethylene, comprising:
   introducing a propylene feed stream to a C3 metathesis reactor;
   contacting the propylene with a metathesis catalyst in the C3 metathesis reactor to convert the propylene to ethylene and 2-butene and recovering an effluent from the C3 metathesis reactor;
   separating the effluent in a fractionation system to recover an ethylene product fraction, a C3 fraction, a C4 fraction, and a C5+ fraction;
   feeding all or a portion of the C3 fraction to the C3 metathesis reactor to produce additional ethylene;
   feeding the C4 fraction to a C4 isomerization/metathesis reaction zone;
   converting the C4 fraction in the C4 isomerization/metathesis reaction zone by: (i) isomerization of a portion of the 2-butenes to 1-butene, (ii) metathesis of the 1-butene and 2-butene to produce propylene and 2-pentene, and/or (iii) autometathesis of the 1-butene to produce ethylene and 3-hexene;
recovering an effluent from the C4 isomerization/metathesis reaction zone, the effluent comprising ethylene, propylene, butenes, pentenes, and hexenes; and
feeding the effluent from the C4 isomerization/metathesis reaction zone to the fractionation system.

2. The process of claim 1, further comprising feeding at least a portion of the C5+ fraction to the C3 metathesis reactor.

3. The process of claim 2, wherein the effluent from the C3 metathesis reactor comprise C7+ olefins, the process further comprising purging a portion of the C5+ fraction.

4. The process of claim 2, further comprising isomerizing 2-pentene and 3-hexene in the C3 metathesis reaction zone to produce 1-pentene and 1-hexene.

5. The process of claim 1, further comprising withdrawing a portion of the C3 fraction as a C3 product fraction.

6. The process of claim 1, further comprising feeding a mixed C4 fraction comprising n-butenes to the C4 isomerization/metathesis reaction zone.

7. The process of claim 1, wherein the C4 isomerization/metathesis reaction zone comprises an isomerization reactor for isomerizing the 2-butene to 1-butene, a C4 superfractionator for separating a 1-butene fraction from a 2-butene fraction, and a metathesis reactor for converting the 1-butene via autometathesis to ethylene and 3-hexene and for converting 1-butene and 2-butene via metathesis to propylene and 2-pentene.

8. The process of claim 7, further comprising feeding at least a portion of the 2-butene fraction recovered in the C4 fractionator to the isomerization reactor.

9. The process of claim 1, further comprising:
feeding hydrogen and a mixed C5 stream to a decyclopentenizer to selectively hydrogenate any cyclopentadiene in the mixed C5 stream and to recover an overheads fraction comprising n-C5 olefins and i-C5 olefins, including 2-pentene, 1-pentene, 3-methyl 1-butene, and 2-methyl-2-butene, and a bottoms stream and/or side draw comprising cyclopentenes;
feeding ethylene and the overheads fraction to a C5 isomerization/metathesis reaction zone for:
isomerizing the 1-pentene to 2-pentene;
isomerizing the 3-methyl-1-butene to 2-methyl-2-butene;
metathesizing the 2-pentene with ethylene to produce 1-butene and propylene; and
metathesizing the 2-methyl-2-butene with ethylene to produce isobutene and propylene;
recovering the metathesis products and unreacted feed components as an effluent from the C5 isomerization/metathesis reaction zone;
fractionating the effluent to recover an ethylene fraction, a propylene fraction, a C4 fraction, and a C5 fraction;
feeding the C5 fraction to the C5 isomerization/metathesis reaction zone.

10. A system for the conversion of propylene to ethylene, comprising:
a flow line for providing propylene from a feed source;
a C3 metathesis reactor for contacting the propylene with a metathesis catalyst to convert the propylene to ethylene and 2-butene and recovering an effluent from the C3 metathesis reactor;
a fractionation system for separating the effluent to recover an ethylene product fraction, a C3 fraction, a C4 fraction, and a C5+ fraction;
a flow line for feeding all or a portion of the C3 fraction to the C3 metathesis reactor;
a flow line for feeding the C4 fraction to a C4 isomerization/metathesis reaction zone;
the C4 isomerization/metathesis reaction zone, for converting the C4 fraction by: (i) isomerization of a portion of the 2-butenes to 1-butene, (ii) metathesis of the 1-butene and 2-butene to produce propylene and 2-pentene, and/or (iii) autometathesis of the 1-butene to produce ethylene and 3-hexene;
a flow line for feeding an effluent from the C4 isomerization/metathesis reaction zone to the fractionation system, the effluent comprising ethylene, propylene, butenes, pentenes, and hexenes.

11. The system of claim 10, further comprising a flow line for feeding at least a portion of the C5+ fraction to the C3 metathesis reactor.

12. The system of claim 11, further comprising a flow line for purging a portion of the C5+ fraction.

13. The system of claim 10, further comprising a flow line for withdrawing a portion of the C3 fraction as a C3 product fraction.

14. The system of claim 10, further comprising a flow line for feeding a mixed C4 fraction comprising n-butenes to the C4 isomerization/metathesis reaction zone.

15. The system of claim 10, wherein the C4 isomerization/metathesis reaction zone comprises an isomerization reactor for isomerizing the 2-butene to 1-butene, a C4 superfractionator for separating a 1-butene fraction from a 2-butene fraction, and a metathesis reactor for converting the 1-butene via autometathesis to ethylene and 3-hexene and for converting 1-butene and 2-butene via metathesis to propylene and 2-pentene.

16. The system of claim 15, further comprising a flow line for feeding at least a portion of the 2-butene fraction recovered in the C4 fractionator to the isomerization reactor.

17. The system of claim 10, further comprising:
a flow line for providing hydrogen and a flow line for providing a mixed C5 stream;
a decyclopentenizer to selectively hydrogenate any cyclopentene and/or cyclopentadiene in the mixed C5 stream and to recover a C5 overheads fraction comprising n-C5 olefins and i-C5 olefins, including 2-pentene, 1-pentene, 3-methyl 1-butene, and 2-methyl-2-butene, and a bottoms stream and/or side draw comprising n-pentanes, i-pentanes, cyclopentene and/or cyclopentane;
a C5 isomerization/metathesis reaction zone receiving an ethylene feed and the C5 overheads fraction, the C5 isomerization/metathesis reaction zone being configure for:
isomerizing the 1-pentene to 2-pentene;
isomerizing the 3-methyl-1-butene to 2-methyl-2-butene;
metathesizing the 2-pentene with ethylene to produce 1-butene and propylene; and
metathesizing the 2-methyl-2-butene with ethylene to produce isobutene and propylene;
a flow line for recovering an effluent from the C5 isomerization/metathesis reaction zone;
a separation system for fractionating the effluent from the C5 isomerization/metathesis reaction zone to recover an ethylene fraction, a propylene fraction, a C4 fraction, and a C5 fraction;
a flow line for feeding the C5 fraction to the C5 isomerization/metathesis reaction zone.

18. The system of claim 17, wherein the ethylene fed to the C5 isomerization/metathesis reaction zone comprises (i) a fresh ethylene feed, (ii) the ethylene fraction, and/or (iii) a portion of the ethylene product fraction.

19. The system of claim 18, further comprising a flow line for feeding the propylene fraction to the C3 metathesis reaction zone.

20. The system of claim 19, further comprising a catalytic distillation reactor for receiving the C4 fraction and concurrently: (a) isomerizing the 1-butene to 2-butene, (b) separating the 2-butene from the isobutene, (c) recovering the isobutene in an overheads fraction, and (d) recovering the 2-butene in a bottoms fraction.

21. The system of claim 20, further comprising a flow line for feeding the bottoms fraction from the catalytic distillation reactor to the C4 isomerizaton/metathesis reaction zone.

22. The system of claim 21, further comprising a flow line for feeding a mixed C4 fraction to the catalytic distillation reactor.

23. The system of claim 19, further comprising a flow line for feeding the C5+ fraction to the C5 isomerization/metathesis reaction zone.

* * * * *